US012661154B2

(12) United States Patent
Biedermann et al.

(10) Patent No.: US 12,661,154 B2
(45) Date of Patent: Jun. 23, 2026

(54) BONE ANCHORING DEVICE

(71) Applicant: BIEDERMANN TECHNOLOGIES GMBH & CO. KG, Donaueschingen (DE)

(72) Inventors: Timo Biedermann, Trossingen (DE); Achim Schünemann, Villingen-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 18/950,862

(22) Filed: Nov. 18, 2024

(65) Prior Publication Data

US 2025/0143753 A1 May 8, 2025

Related U.S. Application Data

(63) Continuation of application No. 17/851,659, filed on Jun. 28, 2022, now Pat. No. 12,171,467.

(Continued)

(30) Foreign Application Priority Data

Jul. 1, 2021 (EP) .................................... 21183181

(51) Int. Cl.
*A61B 17/70* (2006.01)

(52) U.S. Cl.
CPC ...... *A61B 17/7032* (2013.01); *A61B 17/7038* (2013.01)

(58) Field of Classification Search
CPC ............ A61B 17/7032; A61B 17/7035; A61B 17/7037; A61B 17/7038
See application file for complete search history.

(56) References Cited

U.S. PATENT DOCUMENTS 5,575,792 A * 11/1996 Errico ................ A61B 17/7037
606/272
5,647,873 A 7/1997 Errico et al.
(Continued)

FOREIGN PATENT DOCUMENTS

CN 1578645 A 2/2005
CN 1654026 A 8/2005
(Continued)

OTHER PUBLICATIONS

Extended European Search Report for Application No. 15201743.0, dated Jun. 17, 2016, 7 pages.
(Continued)

*Primary Examiner* — Eduardo C Robert
*Assistant Examiner* — Anna V. Little
(74) *Attorney, Agent, or Firm* — Womble Bond Dickinson (US) LLP

(57) ABSTRACT

A bone anchoring device for anchoring a rod to a bone or vertebra includes a receiving part with two legs defining a channel for the rod and a variable configuration member with a first rod contact surface configured to extend axially above a bottom of the channel to contact the rod. When a rod is inserted in the channel, the variable configuration member is adjustable from a first configuration where the first rod contact surface is at a first axial position relative to the receiving part and blocks the rod from contacting a second rod contact surface below the first rod contact surface, and a second configuration where the first rod contact surface is at a second axial position below the first axial position relative to the receiving part to permit the rod to contact the second rod contact surface.

17 Claims, 12 Drawing Sheets

Related U.S. Application Data

(60) Provisional application No. 63/217,426, filed on Jul. 1, 2021.

(56) References Cited

U.S. PATENT DOCUMENTS

| | | | |
|---|---|---|---|
| 5,669,911 A | 9/1997 | Errico et al. | |
| 5,882,350 A | 3/1999 | Ralph et al. | |
| 7,708,762 B2 | 5/2010 | McCarthy et al. | |
| 8,088,152 B2 | 1/2012 | Schumacher | |
| 9,078,705 B2 | 7/2015 | Matthis et al. | |
| 9,168,069 B2 | 10/2015 | Jackson et al. | |
| 9,333,017 B2 | 5/2016 | Biedermann et al. | |
| 9,572,600 B2 | 2/2017 | Biedermann et al. | |
| 9,763,702 B2 | 9/2017 | Schlaepfer et al. | |
| 2003/0158552 A1 | 8/2003 | Jeon et al. | |
| 2004/0225289 A1* | 11/2004 | Biedermann | A61B 17/8605 606/279 |
| 2005/0096653 A1 | 5/2005 | Doubler et al. | |
| 2006/0149235 A1 | 7/2006 | Jackson | |
| 2006/0149240 A1 | 7/2006 | Jackson | |
| 2006/0155278 A1 | 7/2006 | Warnick | |
| 2006/0276791 A1* | 12/2006 | Shluzas | A61B 17/7002 606/301 |
| 2006/0276792 A1 | 12/2006 | Ensign et al. | |
| 2007/0043357 A1 | 2/2007 | Kirschman | |
| 2007/0093827 A1 | 4/2007 | Warnick | |
| 2007/0167949 A1 | 7/2007 | Altarac et al. | |
| 2008/0119857 A1 | 5/2008 | Potash et al. | |
| 2008/0243193 A1 | 10/2008 | Ensign et al. | |
| 2008/0294202 A1 | 11/2008 | Peterson et al. | |
| 2009/0062865 A1 | 3/2009 | Schumacher | |
| 2009/0105716 A1* | 4/2009 | Barrus | A61B 17/7032 606/103 |
| 2009/0105770 A1 | 4/2009 | Berrevoets et al. | |
| 2009/0149887 A1 | 6/2009 | Schlaepfer et al. | |
| 2009/0163961 A1* | 6/2009 | Kirschman | A61B 17/7038 606/103 |
| 2009/0204155 A1 | 8/2009 | Aschmann | |
| 2009/0254125 A1 | 10/2009 | Predick | |
| 2009/0264933 A1* | 10/2009 | Carls | A61B 17/7041 606/264 |
| 2009/0318969 A1 | 12/2009 | Matthis et al. | |
| 2010/0063550 A1 | 3/2010 | Felix et al. | |
| 2010/0160978 A1 | 6/2010 | Carbone | |
| 2010/0234902 A1 | 9/2010 | Biedermann et al. | |
| 2011/0040335 A1* | 2/2011 | Stihl | A61B 17/8863 606/305 |
| 2012/0179211 A1* | 7/2012 | Biedermann | A61B 17/7037 606/279 |
| 2012/0253408 A1 | 10/2012 | Timm | |
| 2012/0253409 A1* | 10/2012 | Peterson | A61B 17/7037 606/305 |
| 2012/0330364 A1 | 12/2012 | Jacofsky et al. | |
| 2013/0096622 A1* | 4/2013 | Biedermann | A61B 17/70 606/279 |
| 2013/0123861 A1 | 5/2013 | Biedermann et al. | |
| 2013/0131734 A1 | 5/2013 | Longtain et al. | |
| 2013/0197586 A1 | 8/2013 | Matthis et al. | |
| 2013/0338721 A1 | 12/2013 | Biedermann et al. | |
| 2013/0345761 A1 | 12/2013 | Biedermann et al. | |
| 2014/0025119 A1 | 1/2014 | Biedermann et al. | |
| 2014/0066986 A1 | 3/2014 | Biedermann et al. | |
| 2014/0142634 A1 | 5/2014 | Schlaepfer et al. | |
| 2015/0119940 A1 | 4/2015 | Jackson et al. | |
| 2015/0196337 A1* | 7/2015 | Biedermann | A61B 17/7032 606/305 |
| 2015/0196338 A1 | 7/2015 | Biedermann et al. | |
| 2016/0038204 A1 | 2/2016 | Biedermann et al. | |
| 2016/0135847 A1 | 5/2016 | Biedermann et al. | |
| 2016/0262816 A1* | 9/2016 | Doubler | A61B 17/8605 |
| 2017/0172630 A1 | 6/2017 | Biedermann et al. | |
| 2017/0340360 A1 | 11/2017 | Schlaepfer et al. | |
| 2018/0153600 A1 | 6/2018 | Koller et al. | |
| 2018/0289398 A1* | 10/2018 | Samuel | A61B 17/8605 |
| 2018/0368889 A1 | 12/2018 | Cole | |
| 2019/0209214 A1* | 7/2019 | Biedermann | A61B 17/7035 |
| 2019/0298419 A1* | 10/2019 | Biedermann | A61B 17/7032 |
| 2021/0033036 A1 | 2/2021 | Andersson et al. | |
| 2021/0330362 A1 | 10/2021 | Biedermann et al. | |

FOREIGN PATENT DOCUMENTS

| | | | | |
|---|---|---|---|---|
| CN | 1784181 A | 6/2006 | | |
| CN | 103222890 A | 7/2013 | | |
| EP | 0 837 656 A1 | 4/1998 | | |
| EP | 1222899 A2 | 7/2002 | | |
| EP | 1726264 A1 | 11/2006 | | |
| EP | 1 743 584 A1 | 1/2007 | | |
| EP | 2022424 A1 | 2/2009 | | |
| EP | 2 070 485 A1 | 6/2009 | | |
| EP | 2 221 012 A1 | 8/2010 | | |
| EP | 2 591 738 A1 | 5/2013 | | |
| EP | 2 674 123 A1 | 12/2013 | | |
| EP | 2 687 171 A1 | 1/2014 | | |
| EP | 2732782 A1 | 5/2014 | | |
| EP | 2829243 A1 | 1/2015 | | |
| EP | 2 687 172 B1 | 3/2015 | | |
| EP | 2851021 A1 | 3/2015 | | |
| EP | 2893890 A1 | 7/2015 | | |
| EP | 3 437 576 A1 | 2/2019 | | |
| EP | 3 501 436 A1 | 6/2019 | | |
| EP | 3 695 796 A1 | 8/2020 | | |
| EP | 3 900 654 A1 | 10/2021 | | |
| JP | 2009-142655 A | 7/2009 | | |
| JP | 2013-255794 | 12/2013 | | |
| JP | 2014-018664 A | 2/2014 | | |
| WO | WO 97/02786 A1 | 1/1997 | | |
| WO | WO 2006/116437 A2 | 11/2006 | | |
| WO | WO-2006119271 A2 * | 11/2006 | | A61B 17/7037 |
| WO | WO-2006127992 A2 * | 11/2006 | | A61B 17/7037 |
| WO | WO 2010/062736 A1 | 6/2010 | | |

OTHER PUBLICATIONS

Extended European Search Report for Application No. 15190858.9, issued on Apr. 13, 2016, 10 pages.

Extended European Search Report issued by the EPO for EP 14180588.7 on Feb. 27, 2015, 6 pages.

Extended European Search Report for Application No. 21183181.3, dated Jan. 5, 2022, 9 pages.

\* cited by examiner

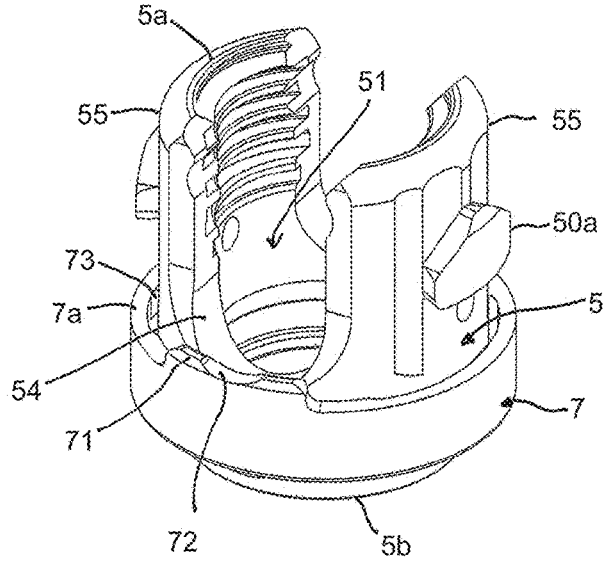
Fig.15
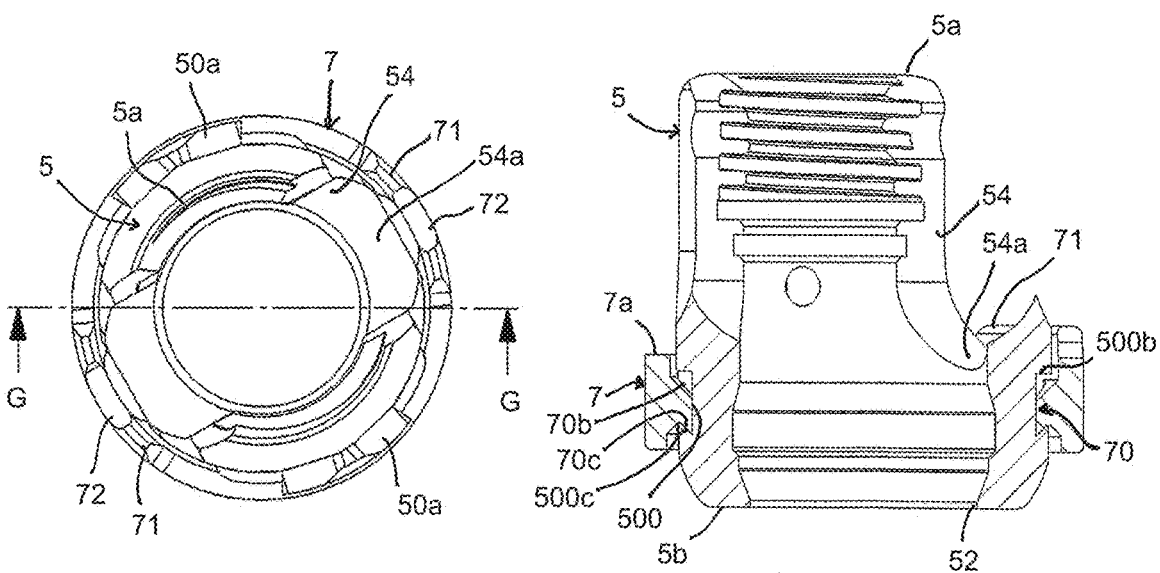
Fig. 16
Fig. 17

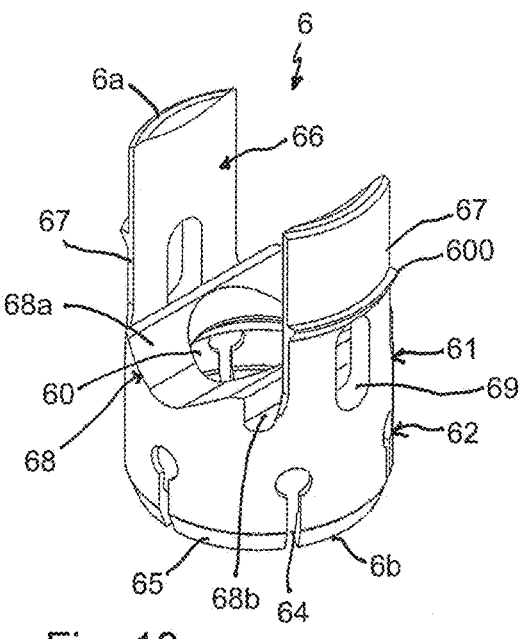
Fig. 18
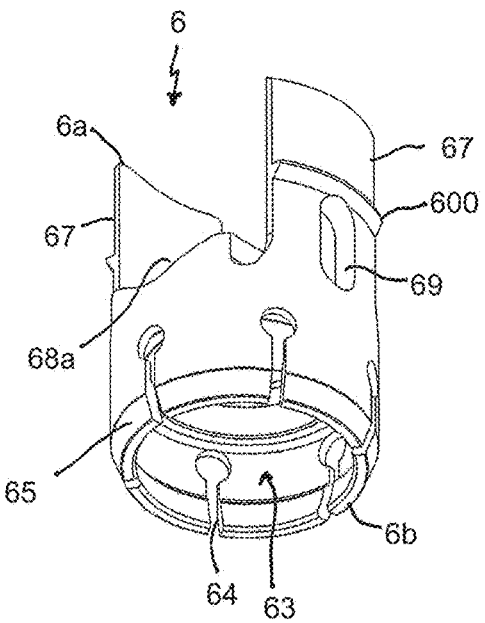
Fig. 19
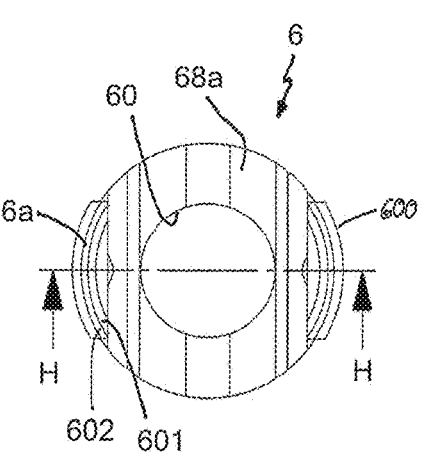
Fig. 20
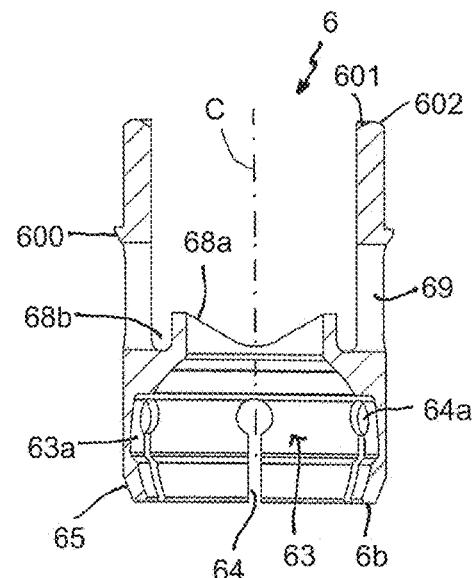
Fig. 21
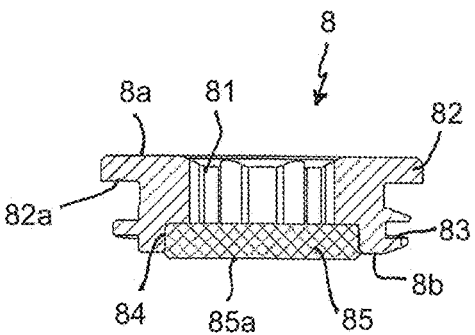
Fig. 22
Fig. 23

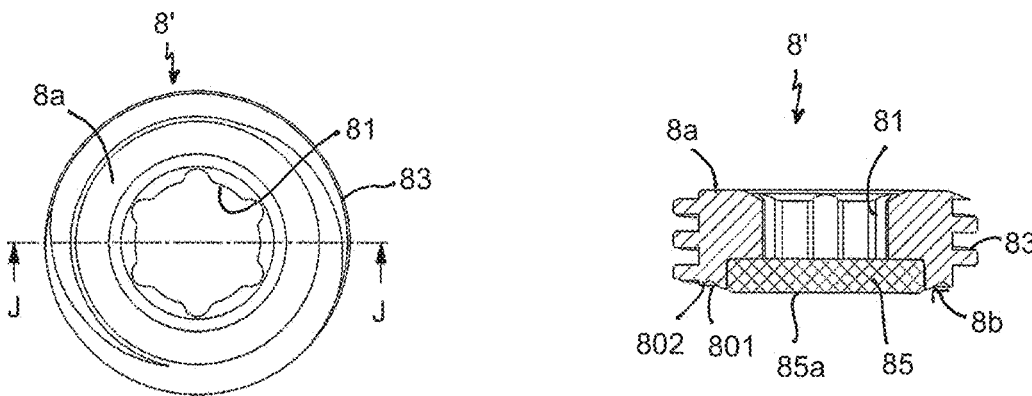
Fig. 25                                    Fig. 26
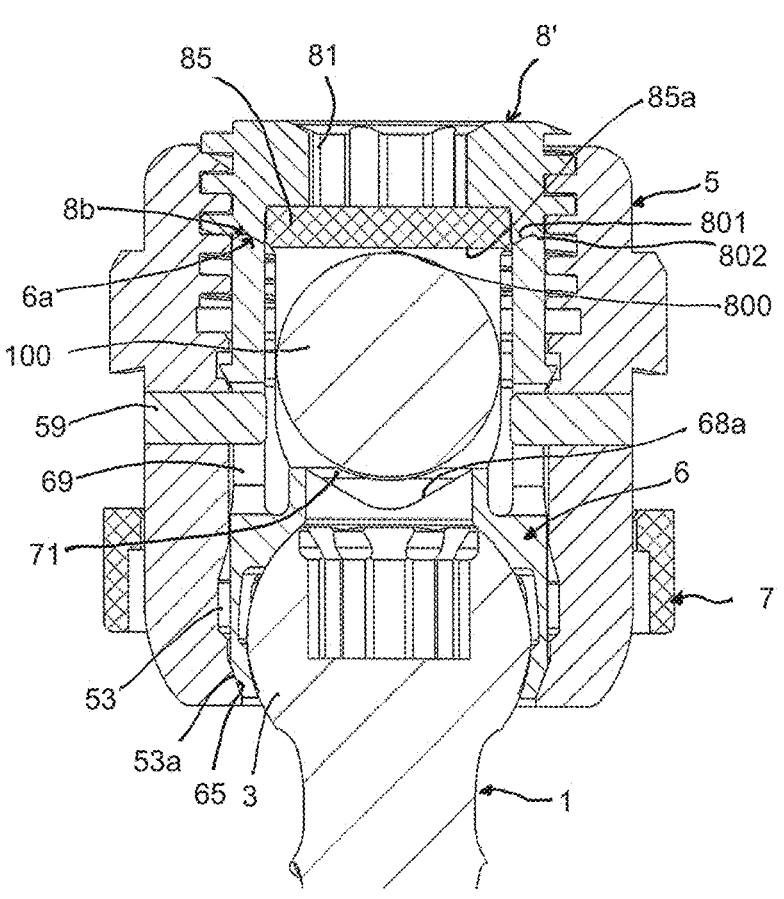
Fig. 27

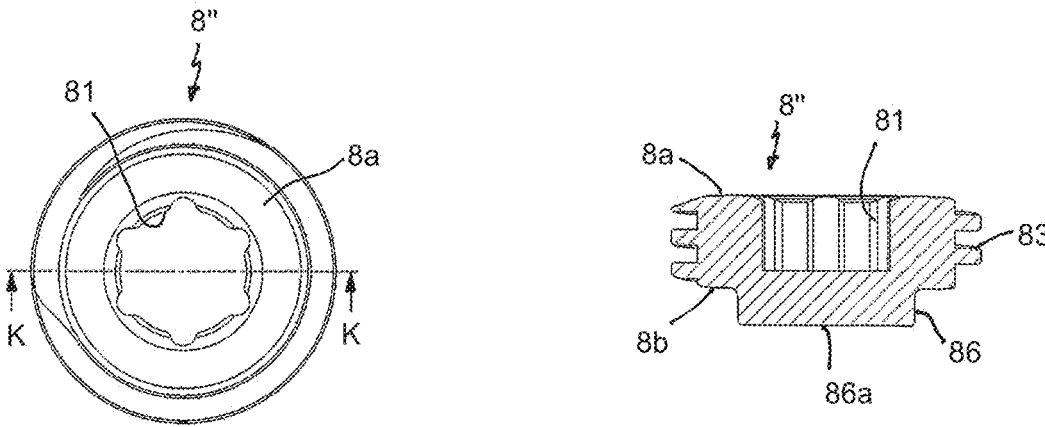
Fig. 28                                    Fig. 29
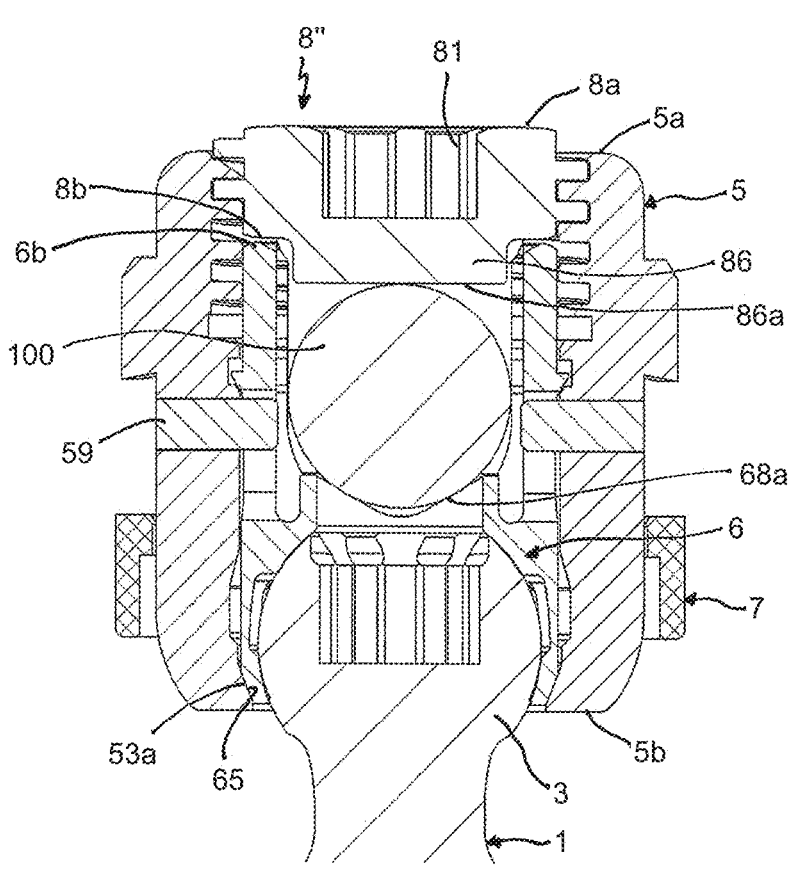
Fig. 30

BONE ANCHORING DEVICE

CROSS-REFERENCE TO RELATED APPLICATION(S)

This application is a continuation of U.S. patent application Ser. No. 17/851,659, filed Jun. 28, 2022, which claims priority to and the benefit of U.S. Provisional Patent Application No. 63/217,426, filed Jul. 1, 2021, the contents of which are hereby incorporated by reference in their entirety, and claims priority from European Patent Application EP 21 183 181.3, filed Jul. 1, 2021, the contents of which are hereby incorporated by reference in their entirety.

BACKGROUND

Field

The application relates to a bone anchoring device that can be used together with a stabilization rod in multiple ways. The bone anchoring device is particularly applicable to the correction of deformities of the spine, more particularly of the pediatric spine. The bone anchoring device can also be useful in degenerative spinal surgery, in particular in dynamic stabilization or hybrid constructs.

Description of Related Art

For the treatment of early onset scoliosis of the pediatric spine, it is known to use growing rods. These are spinal implants fixed above and below the abnormally curved portion of the spine to correct the curvature in a first step to some extent. Thereafter, the rods are prolonged in further correction surgeries to adapt them to the growth of the spine.

Systems, devices, and methods for stabilization of the spinal column, in particular for treating infantile or juvenile scoliosis are known, for example, from U.S. Pat. No. 7,708,762 B2. A system described there includes an elongate support member and a plurality of anchor members configured for anchoring to respective vertebrae. A first of the anchor members is engaged to the elongate support member in a manner that substantially prevents axial movement of the support member relative to the first anchor member, and a second of the anchor members is engaged to the support member in a manner that allows substantially unconstrained axial movement of the support member relative to the second anchor member. With the system and device the number and/or frequency of adjustments of the stabilization system to accommodate for continued growth of a patient's spinal column, particularly in pediatric patients, can be reduced.

EP 3 695 796 A1 describes an anchoring assembly for anchoring a rod to a bone or a vertebra that permits selection between rods with different diameters when using a bone anchoring device, and simultaneously permitting selection between different locking mechanisms.

SUMMARY

It is an object of the invention to provide a bone anchoring device and a system including a bone anchoring device and at least two fixation members that provides a plurality of possibilities of using the bone anchoring device and/or the system together with a rod.

According to an aspect of the invention, a bone anchoring device for anchoring a rod to a bone or vertebra via a shank to be anchored in bone includes a receiving part connectable or connected to the shank, the receiving part including two legs that define a channel for the rod and a variable configuration member. The variable configuration member is configured to allow the bone anchoring device to provide a variable functionality. The variable configuration member provides a first rod contact surface that is arranged outside of the receiving part and wherein in the receiving part a second rod contact surface is provided. The variable configuration member is adjustable from a first configuration in which an inserted rod can contact the first rod contact surface, and a second configuration in which an inserted rod is supported by the second rod contact surface and preferably also by the first rod contact surface. Preferably, the variable configuration member is an outer ring extending around the receiving part. Further preferably, a change from the first configuration to the second configuration can be effected by pressure exerted by the rod onto the first rod contact surface.

In the first configuration, the first rod contact surface and the second rod contact surface have a first positional relationship relative to each other and in the second configuration, the first rod contact surface and the second rod contact surface may have a second positional relationship relative to each other different from the first positional relationship. Preferably, a change between the first positional relationship and the second positional relationship involves a change in an axial position of at least one of the rod contact surfaces. Preferably, the change in the positional relationship involves a deformation of the variable configuration member. More preferably, an overall axial position of the variable configuration member remains the same during the change of position of the first rod contact surface.

The bone anchoring device can be employed as a bone anchoring device that can be fixed to the rod and as a bone anchoring device that is slidable with respect to the rod to permit a positional change of the bone anchoring device relative to the rod when implanted. Thus, the bone anchoring device can be used as a growing construct that allows the spine to grow while correcting a scoliotic deformity. Whether a fixed or a slidable connection is established can be easily selected by using an appropriate fixation member. This provides an improved or alternative way of treating, in particular, spinal deformities, and more particularly deformities in the pediatric or juvenile spine, or in degenerative spinal surgery, in particular, in dynamic stabilization or hybrid construct applications.

According to a further aspect of the invention, the bone anchoring device is a polyaxial bone anchoring device. This means that the receiving part is pivotably coupled to a head provided at an end of the shank, and a pressure member can be arranged in the receiving part that is configured to exert pressure onto the head. In the polyaxial bone anchoring device, the second rod contact surface is provided on the pressure member that is arranged in the receiving part.

In particular, the bone anchoring device may be a bottom-loading bone anchoring device, in which the head of the bone anchoring element is inserted through the bottom end of the receiving part. However, the bone anchoring device may also be a top-loading bone anchoring device, in which the anchoring element is inserted from the top end of the receiving part.

A first fixation member functions as a closure member for the rod channel. The first fixation member is configured to be insertable into the receiving part in a limited manner so that the head is still freely pivotable and the rod is displaceable in the receiving part. With a second fixation member, it is possible to clamp or substantially lock the head while the rod is still freely displaceable within the receiving part. A third fixation member is configured to exert pressure only onto the rod to finally lock the rod and the head.

According to a still further aspect of the invention, the bone anchoring device is a monoaxial bone anchoring device, in which the shank is fixedly connected to the receiving part. The second rod contact surface is provided at the receiving part itself. With the first fixation member, the rod remains movable in the rod channel. With the third fixation member, the rod can be fixed in the rod channel.

The bone anchoring device according to embodiments of the invention is also configured to be used with rods of different diameters.

By interchanging the fixation member and/or the type of the bone anchoring device, the rod and/or the head can be clamped or kept movable. Hence, the function of the bone anchoring device can be easily defined and/or changed. Thus, the bone anchoring device together with at least two fixation members provides a modular system that permits different locking configurations of the head and/or the rod by selecting an appropriate fixation member.

BRIEF DESCRIPTION OF THE DRAWINGS

Further features and advantages of the invention will become apparent from the description of embodiments by means of the accompanying drawings. In the drawings:

FIG. 15 shows a perspective view from a top of the receiving part of FIGS. 5 to 9 with the outer ring of FIGS. 10 to 14 mounted thereon.

FIG. 16 shows a top view of the receiving part with the mounted outer ring of FIG. 15.

FIG. 17 shows a cross-sectional view of the receiving part with the mounted outer ring of FIGS. 15 and 16, the cross-section taken in a plane along line G-G in FIG. 16.

FIG. 18 shows a perspective view from a top of a pressure member of the bone anchoring device shown in FIGS. 1 to 4.

FIG. 19 shows a perspective view from a bottom of the pressure member of FIG. 18.

FIG. 20 shows a top view of the pressure member of FIGS. 18 and 19.

FIG. 21 shows a cross-sectional view of the pressure member of FIGS. 18 to 20, the cross-section taken in a plane along line H-H in FIG. 20.

FIG. 22 shows a top view of the first fixation member of the polyaxial bone anchoring device of FIGS. 1 to 4.

FIG. 23 shows a cross-sectional view of the first fixation member of FIG. 22, the cross-section taken in a plane along line I-I in FIG. 22.

FIG. 24a to FIG. 24f show steps of assembling the polyaxial bone anchoring device of FIGS. 1 to 4 and using the bone anchoring device with a rod, wherein FIG. 24f is an enlarged view of a detail of FIG. 24e.

FIG. 25 shows a top view of a second fixation member of the system shown in FIG. 1.

FIG. 26 shows a cross-sectional view of the second fixation member of FIG. 25, the cross-section taken in a plane along line J-J in FIG. 25.

FIG. 27 shows a cross-sectional view of the polyaxial bone anchoring device of FIG. 1 with the second fixation member of FIGS. 25 and 26, the cross-section taken in a plane perpendicular to the longitudinal axis of the rod channel and extending through centers of the legs of the receiving part.

FIG. 28 shows a top view of a third fixation member of the system shown in FIG. 1.

FIG. 29 shows a cross-sectional view of the third fixation member of FIG. 28, the cross-section taken in a plane along line K-K in FIG. 28.

FIG. 30 shows a cross-sectional view of the polyaxial bone anchoring device of FIG. 1 with the third fixation member of FIGS. 28 and 29, the cross-section taken in a plane perpendicular to the longitudinal axis of the rod channel and extending through centers of the legs of the receiving part.

DETAILED DESCRIPTION

Figure 1:
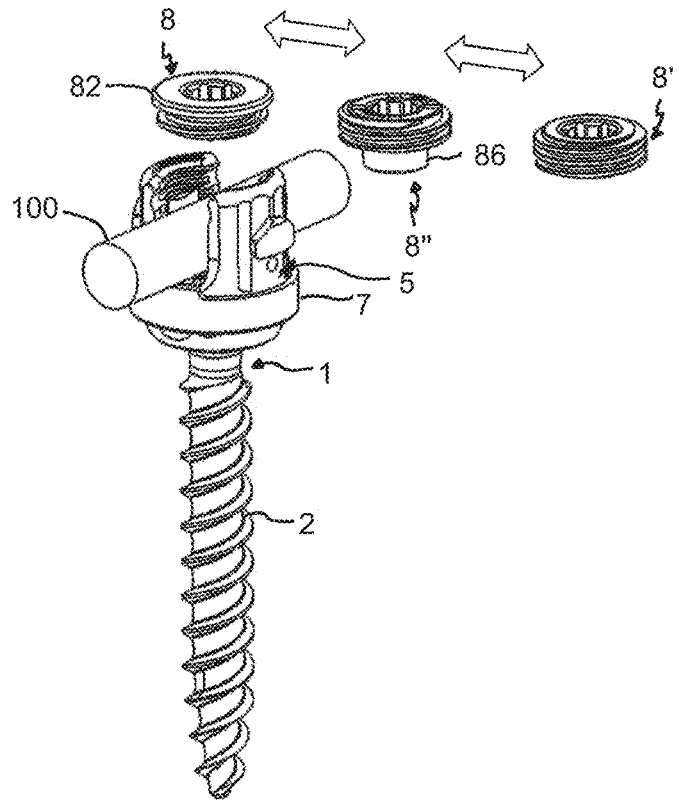
FIG. 1 shows a perspective view of an embodiment of a system including a bone anchoring device and different interchangeable fixation members.
Figure 2:
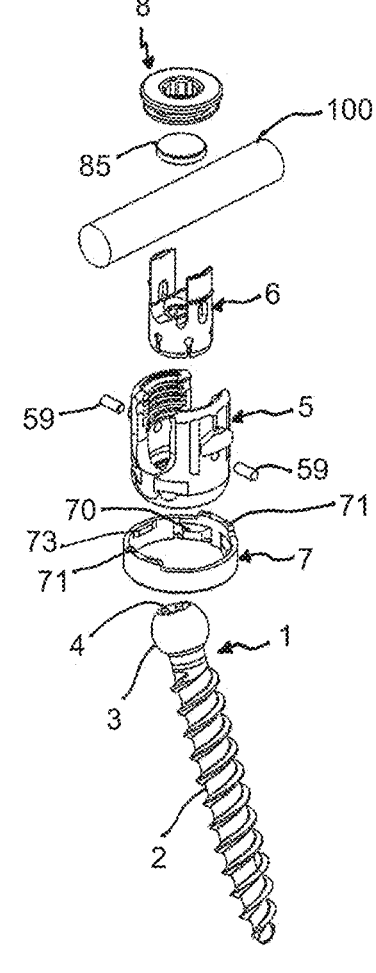
FIG. 2 shows a perspective exploded view of a first embodiment of the bone anchoring device shown in FIG. 1 with a first fixation member.
Figure 3:
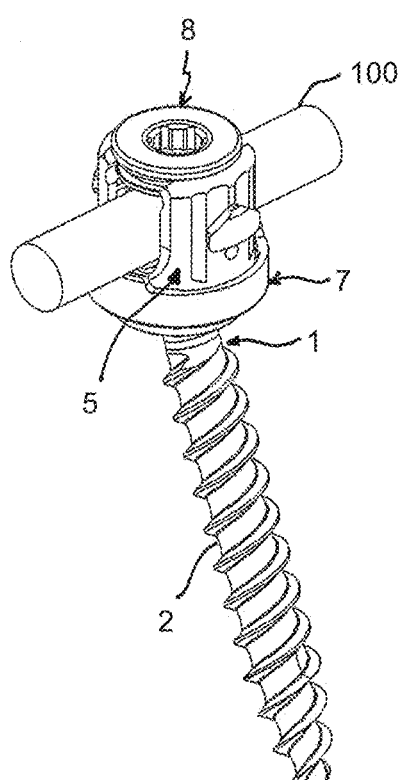
FIG. 3 shows a perspective view of the bone anchoring device of FIGS. 1 and 2 in an assembled state.
Figure 4:
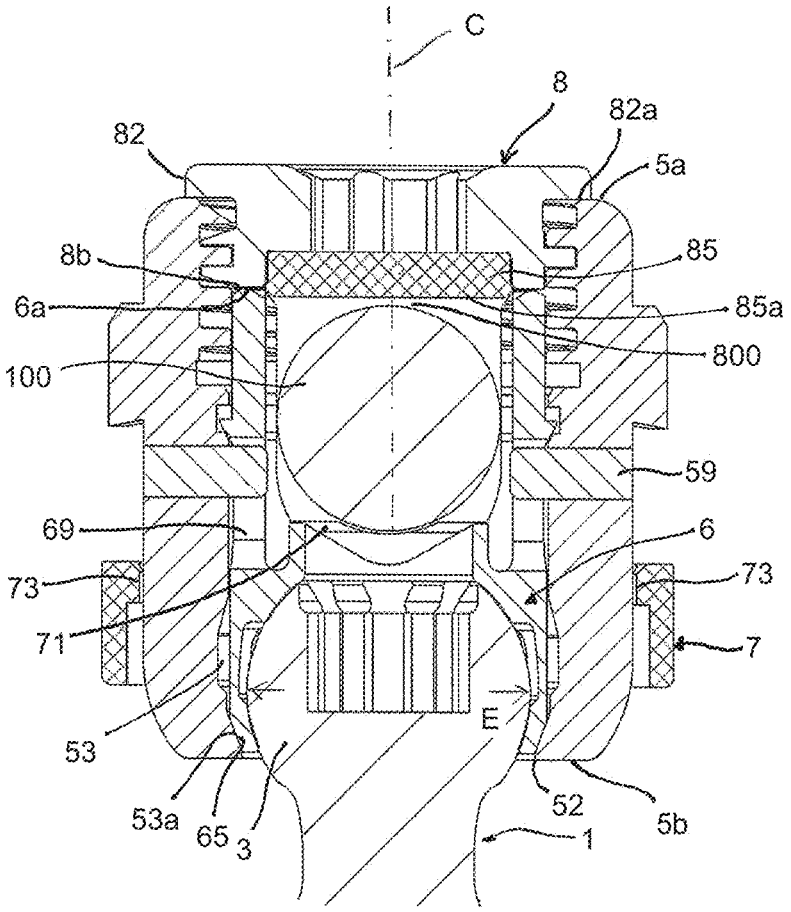
FIG. 4 shows a cross-sectional view of the bone anchoring device of FIGS. 1 to 3, the cross-section taken in a plane perpendicular to a longitudinal axis of a rod channel and extending through centers of legs of a receiving part of the bone anchoring device.
Figures 5, 6, 7, 8, 9:
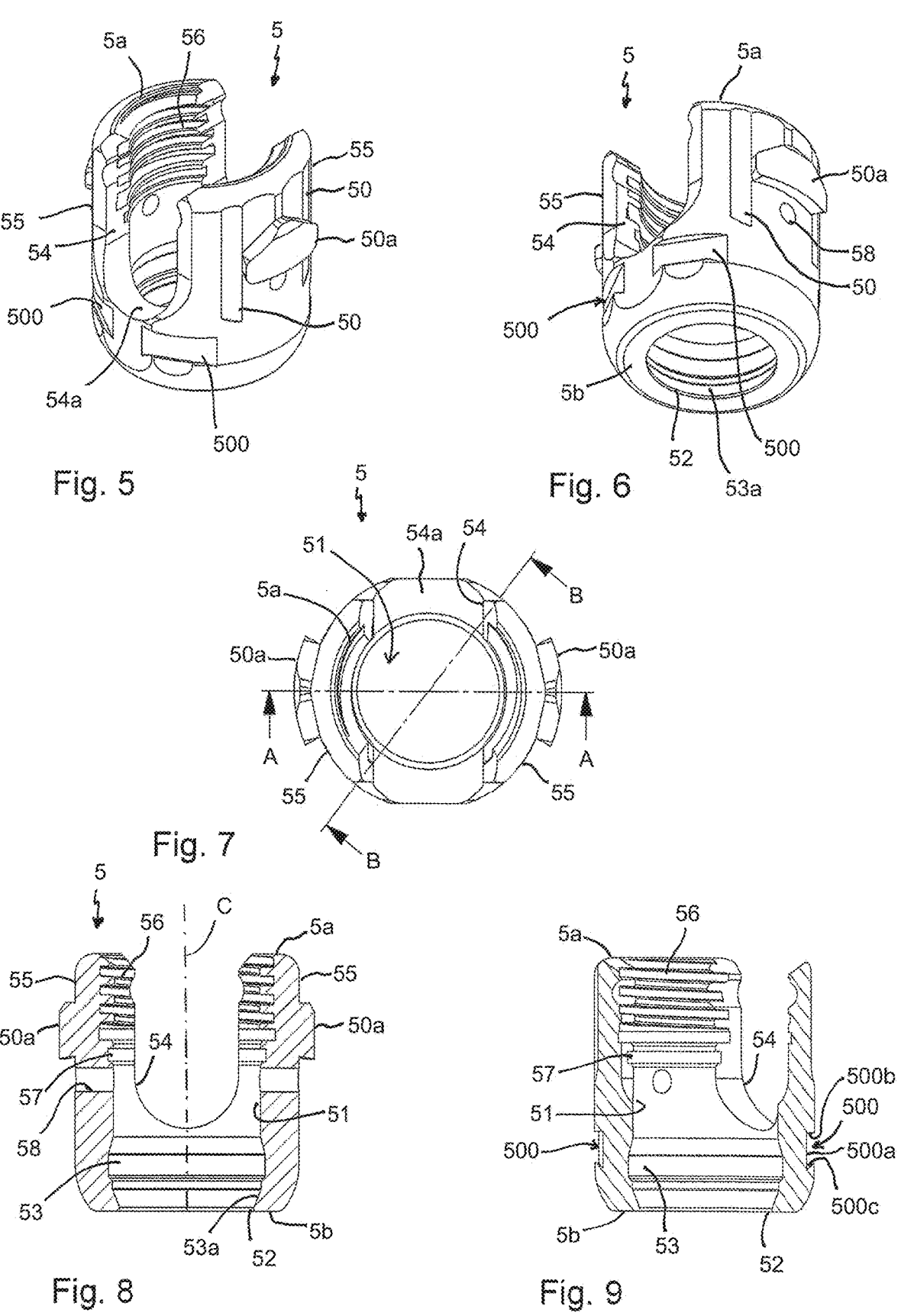
FIG. 5 shows a perspective view from a top of the receiving part of the bone anchoring device of FIGS. 1 to 4.
FIG. 6 shows a perspective view from a bottom of the receiving part of FIG. 5.
FIG. 7 shows a top view of the receiving part of FIGS. 5 and 6.
FIG. 8 shows a cross-sectional view of the receiving part of FIGS. 5 to 7, the cross-section taken in a plane along line A-A in FIG. 7.
FIG. 9 shows a cross-sectional view of the receiving part of FIGS. 5 to 8, the cross-section taken in a plane along line B-B in FIG. 7.
Figure 10:
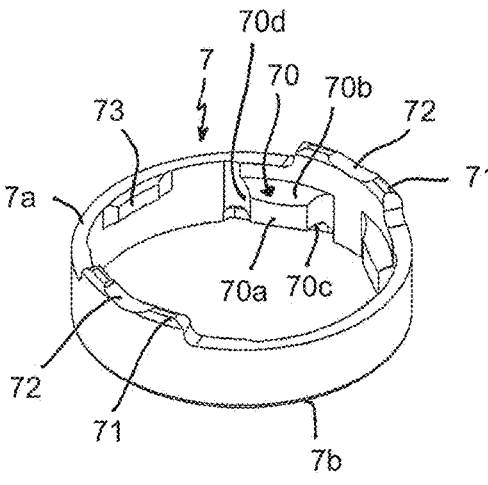
FIG. 10 shows a perspective view from a top of a variable configuration member in the form an outer ring of the bone anchoring device of FIGS. 1 to 4.
Figure 11:
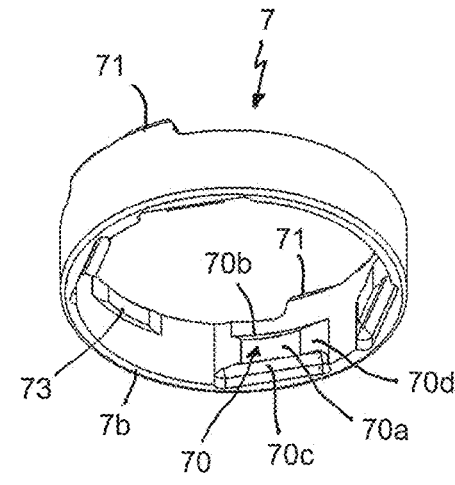
FIG. 11 shows a perspective view from a bottom of the outer ring of FIG. 10.
Figure 12:
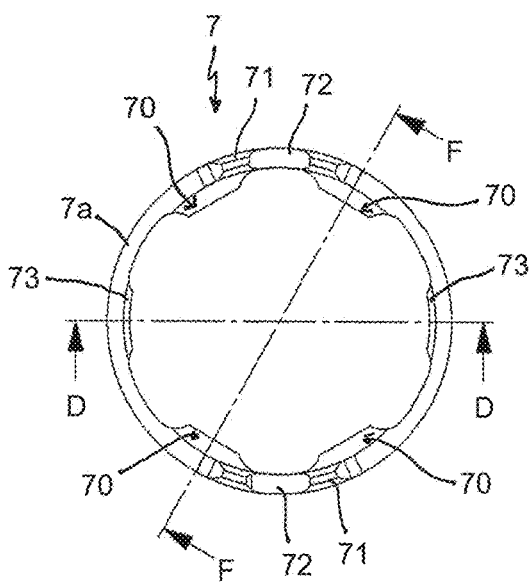
FIG. 12 shows a top view of the outer ring of FIGS. 10 and 11.
Figure 13:
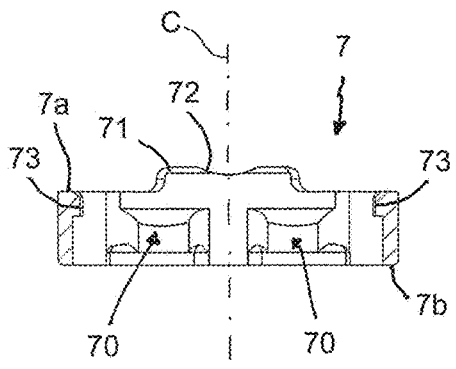
FIG. 13 shows a cross-sectional view of the outer ring of FIGS. 10 to 12, the cross-section taken in a plane along line D-D in FIG. 12.
Figure 14:
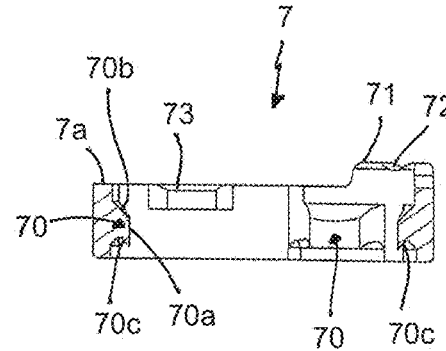
FIG. 14 shows a cross-sectional view of the outer ring of FIGS. 10 to 13, the cross-section taken in a plane along line F-F in FIG. 12.

Referring to FIGS. 1 to 4, a bone anchoring device according to a first embodiment is a polyaxial axial bone anchoring device. The bone anchoring device includes a bone anchoring element 1 having a shank 2 with a threaded portion and a head 3. The head 3 has a spherically-shaped outer surface portion and, on its side opposite to the shank 2, a recess 4 for engagement with a tool. A receiving part 5 is provided for coupling the bone anchoring element 1 to a rod 100. In the receiving part 5, a pressure member 6 is arranged to exert pressure onto the head 3 of the bone anchoring element 1. Additionally, the bone anchoring device includes a variable configuration member in the form of an outer ring 7 that is configured to be mounted around the receiving part 5. The outer ring 7 is further configured to provide a support for the rod 100 when the rod 100 is placed into the receiving part 5.

Moreover, the bone anchoring device may further include a first fixation member 8 that is configured to cooperate with the receiving part 5 to secure the rod 100 in the receiving part 5. In addition, a second fixation member 8' and a third fixation member 8" may be provided wherein the three fixation members are all interchangeably usable with the bone anchoring device. The second fixation member 8' is configured to cooperate with the receiving part 5, such that the head 3 is clamped or locked and the rod 100 remains movable along an axis of the rod. The third fixation member 8" is configured to cooperate with the receiving part 5, such that the rod 100 and the head 3 can be locked simultaneously. Thus, the polyaxial bone anchoring device and the first, the second, and the third fixation members form a modular system, in particular, a modular system that can realize different functions for the polyaxial bone anchoring device.

The rod 100 may be a cylindrical straight rod that is configured to stabilize bone parts or vertebrae connected through the rod. Preferably, the surface of the rod 100 is smooth, at least to an extent such that the rod 100 can slide along a fixation member when the rod touches the fixation member while not being fixed. It shall be noted that the rod is not limited to a straight rod as depicted in the embodiments, but can be any elongate stabilization member that is configured to be displaceably, in particular slidably, receivable in the receiving part 5.

Turning now to FIGS. 5 to 9, the receiving part 5 will be described in greater detail. The receiving part 5 has a first end or top end 5a and a second end or bottom end 5b opposite to the top end 5a. The receiving part may have a substantially cylindrical outer shape, with a central longitudinal axis C extending through the top end 5a and the bottom end 5b. Coaxially with the central axis C, a passage 51 is provided that extends from the top end 5a to the bottom end 5b and forms an opening 52 at the bottom end 5b. At a distance from the top end 5a, the passage 51 widens into an accommodation space 53 that is configured to receive the head 3 and at least a portion of the pressure member 6. Adjacent to the opening 52 at the bottom end 5b, the accommodation space 53 narrows towards the opening 52 in a narrowing portion 53a, which may be, for example, a tapered, and more particularly, a conical surface that may cooperate with a corresponding portion of the pressure member 6. A width of the opening 52 may be greater than a greatest width E of the head 3 (FIG. 4), so that the head 3 may be inserted from the bottom end 5b into the accommodation space 53. To enable the insertion of the head 3 from the bottom end 5b, the width of the accommodation space 53 is such that the pressure member 6 can expand therein to permit the insertion of the head 3.

The receiving part 5 further defines a substantially U-shaped recess 54 starting at the top end 5a and extending in the direction of the bottom end 5b, with a bottom 54a at its deepest position. By means of the U-shaped recess 54, two free legs 55 are formed that define a channel for receiving the rod 100.

On an inner surface of the legs 55, an internal thread 56 is formed, which is in the exemplary embodiment a square thread or another flat thread. For cooperation with a portion of the pressure member 6, a circumferential groove 57 may be provided at the inner wall of the legs 55 at a distance from the bottom 54a of the U-shaped recess 54.

In addition, transverse holes 58 may extend through the legs 55, respectively, in a direction perpendicular to the central axis C and at a position approximately at the center of each of the legs 55 in the circumferential direction. The transverse holes 58 may serve for accommodating pins 59 that extend through the holes 58 into the channel. The pins 59 are configured to engage the pressure member 6 to form a securing structure to secure the pressure member 6 against rotation. In addition, the pins 59 may limit an upward movement of the pressure member 6. At an outside of the legs 55, for example, longitudinal recesses 50 and/or attachment projections 50a may be provided for engagement with a tool or an instrument.

At an axial position below the bottom 54a of the substantially U-shaped recess 54 and to the right and to the left of the bottom 54a on either side of the rod channel in a circumferential direction, a holding structure for the outer ring 7 is provided. The holding structure may include grooves 500 for engagement with a portion of the outer ring 7. The grooves 500 extend circumferentially in a portion of the outer surface of the receiving part 5. More specifically, the grooves 500 may have a circumferential length that may be less than half, and more particularly, less than a quarter, of the circumference of the receiving part. Hence, four such grooves may be formed, two on each end of the rod channel.

Each of the grooves 500 has a rectangular contour in a front view and includes an inner wall 500a which is sandwiched between an upper wall 500b that faces towards the bottom end 5b of the receiving part 5 and a lower wall 500c that faces towards the top end 5a of the receiving part 5. The inner wall 500a may be flat, such that a depth of the groove increases from ends of the groove towards a center of the groove in the circumferential direction. The upper wall 500b may be straight, and more particularly may extend substantially perpendicular to the central axis C. The lower wall 500c forms a stop for a portion of the outer ring 7. In greater detail, the lower wall 500c is inclined in a manner such that the lower wall forms an undercut of the groove. This permits engagement with a portion of the outer ring 7 and prevents inadvertent removal or detachment of the outer ring 7 via the lower end 5b of the receiving part 5 once the outer ring 7 has been mounted. When the outer ring 7 engages the grooves 500, the orientation of the outer ring relative to the receiving part is maintained. Thus, the grooves also form a securing structure against inadvertent rotation of the outer ring. While one such groove may be sufficient, preferably for stability reasons, at least two, and more preferably four, such grooves are provided with the described structure.

Referring further to FIGS. 10 to 14, the outer ring 7 has a first end or upper end 7a and an opposite second end or lower end 7b. An inner width of the outer ring 7 is such that the outer ring 7 fits around the receiving part 5 in an axial region between the bottom 54a of the U-shaped recess 54 and the bottom end 5b.

At positions corresponding to the positions of the grooves 500 in the outer surface of the receiving part 5, the outer ring 7 has counterpart holding structures in the form of protrusions 70 that are configured to engage the grooves 500. More specifically, each protrusion 70 has an inner surface 70a that is configured to abut against the inner surface 500a of the groove 500 when the outer ring 7 is mounted to the receiving part 5. An upper surface 70b of the protrusion 70 may be inclined in a manner such that sliding of the outer ring 7 over the receiving part 5 when the outer ring 7 is mounted from the lower end 5b is more easily facilitated. An opposite lower surface 70c of the protrusion 70 is inclined, preferably also having or forming an undercut, in a manner such that the lower surface 70c can snap into the undercut provided by the lower surface 500c of the groove 500, and preferably can hook therein (see FIG. 17). Thus, the lower surface 500c of the groove 500 forms a stop for the outer ring 7 when the outer ring 7 is mounted and moved towards the second end 5b. The sidewalls 70d of the protrusion 70 may be concavely rounded to permit easy entrance into the groove 500. The position of the protrusions 70 in the axial direction and distance of the protrusions 70 from the lower end 7b may be such that, once the protrusions 70 have entered the grooves 500, the protrusions can move slightly in an axial direction in the groove. Corresponding to the grooves 500, four protrusions 70 are formed.

At a circumferential position between two neighboring protrusions 70 in the circumferential direction, an elevation 71 is formed at the upper end 7a of the outer ring 7. Hence, the outer ring 7 has two elevations 71 that are offset by 180°. The elevations 71 are configured to protrude above the bottom 54a of the recess 54 of the receiving part 5 when the outer ring 7 has been mounted to the receiving part 5. A shallow depression 72 may be formed on the upper surface of each elevation 71. The depression 72 functions as a first rod contact surface.

The outer ring 7 may further include stiffening structures 73. The stiffening structures 73 may be formed as protrusions that are offset from each other by 180° and located at circumferential positions approximately in the middle between the elevations 71 and at an axial position preferably adjacent to or close to the upper end 7a of the outer ring 7. The shape of the protrusions may be similar to the shape of the protrusions 70, however the radial thickness of the stiffening structures 73 may be smaller since the stiffening structures 73 do not engage a groove in the receiving part. When pressure is exerted via the rod on the first rod contact surface 72, the outer ring is deformed in a manner such that the ring shape of the outer ring is slightly changed so that the first rod contact surface 72 at the elevations 71 is moved towards the lower end 5b of the receiving part 5. The stiffening structures 73 enable such a defined deformation. Upon relieving the pressure from the rod, the outer ring can assume its original ring shape again.

It shall be noted that the design of the holding structures and of the stiffening structures is not limited to the specific shapes shown, but can have different shapes that result in the same or similar functionality.

An outer width of the outer ring 7 may be such that the outer ring does not or only minimally protrudes beyond the outer surface of the protrusions 50a of the receiving part 5.

The outer ring preferably is made of a material such that the outer ring is flexible or deformable to some extent. In particular, the outer ring 7 is deformable when pressure is exerted onto the first rod contact surface 72. Such a material is preferably a polymer material, more preferably a body-compatible polymer material, such as, for example, polyether ether ketone (PEEK). Due to the material and to the shape, the outer ring may be elastically deformable, i.e., when a load that causes a deformation of the outer ring 7 is relieved, the outer ring 7 can assume its original shape. In addition, the material facilitates sliding of the rod when the rod is on the first rod contact surface 72.

Referring now to FIGS. 18 to 21, the pressure member 6 will be described. The pressure member 6 may be formed as a monolithic part, with a first or upper end 6a and a second or lower end 6b, opposite to the upper end 6a. Adjacent to the upper end 6a, the pressure member 6 includes a substantially cylindrical first portion 61 that is adapted to be received in the passage 51 of the receiving part 5 and to move therein in an axial direction. Adjacent to the lower end 6b, a substantially cylindrical second portion 62 is formed that is configured to extend at least partially into the accommodation space 53 of the receiving part 5. Further, adjacent to the lower end 6b, a head receiving recess 63 that may be adapted to the spherical shape of the head 3 is formed in the second portion 62. The head receiving recess 63 may be sized so as to frictionally hold the head 3 of the bone anchoring element 1 therein. A widened cylindrical portion 63a in the head receiving recess 63 may enhance flexibility of the head receiving recess 63 and may facilitate pivoting of the head 3. Due to a plurality of longitudinal slits 64 that are open to the second end 6b and that preferably have widened end portions 64a, the second portion 62 is rendered flexible. Adjacent to the lower end 6b, the outer surface of the second portion 62 includes a narrowing portion 65, preferably a tapered and more preferably a conically-tapered portion, that is configured to cooperate with the narrowing portion 53a of the accommodation space 53. By means of the cooperating surfaces 65, 53a of the pressure member 6 and of the receiving part 5, respectively, the flexible second portion 62 of the pressure member 6 can be compressed to clamp or lock the head 3 in the head receiving recess 63.

Adjacent to the upper end 6a, a substantially U-shaped recess 66 forms two open legs 67 that preferably have substantially flat inner walls. The substantially U-shaped recess 66 has an elevated base 68 with a surface 68a that has a substantially V-shaped contour with a rounded bottom. The surface 68a forms a second rod contact surface that is in this embodiment configured to receive rods of different diameters thereon. Moreover, the support surface 68a lies at an axial height with respect to the upper end 6a of the pressure member 6 such that, when a rod having a greatest possible diameter that can be accommodated by the pressure member rests on the second rod contact surface 68a, the upper end 6a of the pressure member, and more specifically of the legs 67, projects above the upper surface of the rod. By means of the elevated base 68, two grooves 68b are formed between the right and the left side of the elevated base 68 and the legs 67. Thereby the legs 67 may be slightly radially flexible. The end surface at the upper end 6a of the pressure member 6 may have a substantially roof-shaped cross-section, with an inclined inner surface 601 and an inclined outer surface 602 that may be shorter than the inclined inner surface 601.

The pressure member 6 further includes a coaxial bore 60 that serves for accessing the recess 4 of the head 3 with a tool. In addition, at approximately a center of each of the legs 67 in a circumferential direction, an axially elongate hole 69 is provided that is configured to be engaged by the pins 59. The corporation between the pins 59 and the elongate holes 69 prevents rotation of the pressure member 6 with respect to the receiving part 5. Furthermore, the pins 59 form a stop against an upward movement of the pressure member 6, for example, when the head 3 is inserted through the lower opening 52 of the receiving part 5 into the head receiving recess 63 of the pressure member 6. Above the elongate recesses 69, circumferentially extending projections 600 with a substantially flat upper surface may be provided that are configured to engage the groove 57 of the receiving part 5. By means of this, a pre-locking position of the pressure member 6 in the receiving part 5 can be secured, as further described below.

Referring to FIGS. 22 and 23, the first fixation member 8 is formed as a set screw with an upper end 8*a* and an opposite lower end 8*b*. In the upper end 8*a*, a tool-receiving recess 81 is provided that may have, for example, a torx-shape. In addition, at the upper end 8*a*, a circumferentially extending flange 82 is formed that protrudes in a radial direction beyond the outer thread 83 of the set screw. At the lower end 8*b*, a recess 84 receives an insert 85. The insert 85 may be disc-shaped with a substantially circular outer contour that is held, for example, via a press-fit connection in the recess 84. An axial thickness of the disc-shaped insert 85 may be such that a lower surface 85*a* of the insert 85 protrudes slightly out of the lower end 8*b* of the first fixation member 8. An outer diameter of the insert 85 is slightly smaller than the distance between the inner surfaces of the legs 67 of the pressure member 6, such that the insert can extend between the legs 67, preferably without exerting a force onto the pressure member 6. The insert 85 is preferably made of a material that facilitates sliding of the rod along the lower surface 85*a*. More specifically, the insert 85 may be made of a polymer, particularly of a body-compatible polymer, such as PEEK.

The flange 82 functions as a stop to limit the advancement of the first fixation member 8 between the legs 55. An axial length of the first fixation member 8 is such that when the first fixation member 8 is inserted between the legs 55 of the receiving part 5 and screwed downward until the flange 82 abuts against the top end 5*a* of the receiving part, neither the lower surface 85*a* nor the lower end 8*b* of the first fixation member 8 exerts a downward axial force onto the pressure member 6. In other words, a position of the pressure member 6 remains unaffected by the first fixation member 8 when the flange 82 abuts against the top end 5*a* of the receiving part 5. Preferably, there is a small gap between the upper end 6*a* of the pressure member 6 and the surface at the lower end 8*b* of the first fixation member 8. Moreover, the axial length of the first fixation member is such that there is a gap 800 between the upper surface of the rod 100 and the lower surface 85*a* of the first fixation member 8. The size of the gap 800 depends on the size of the rod. In some cases, the gap is so small so that the rod 100 is configured to slide along the lower surface 85*a*. In clinical use, if the gap 800 is large enough, the rod may even be able to move freely without contacting the first fixation member 8 or the pressure member 6. Alternatively, the axial length of the portion of first fixation member 8 that protrudes into the rod channel and/or the diameter of the rod may be such that the rod slides along the lower side of the first fixation member and on the first rod contacting surface 72 of the outer ring 7.

The bone anchoring element, the receiving part, and the pressure member, as well as the rod and the fixation member, may be made of the same or of different materials, preferably of a bio-compatible material such as titanium or stainless steel, or of a bio-compatible alloy, such as NiTi alloys, for example Nitinol, or of a bio-compatible plastic material, for example, polyether ether ketone (PEEK).

The receiving part 5, the pressure member 6, and the outer ring 7 usually are pre-assembled before attaching them to a bone anchoring element and/or a rod. For assembly, the pressure member 6 is inserted through the top end 5*a* into the receiving part, such that the head receiving recess 63 extends into the accommodation space 53. The second rod contact surface 68*a* of the pressure member 6 is aligned with the U-shaped recess 54. The pressure member 6 is secured against rotation by the pins 59 which extend through the through-holes 58 of the receiving part into the elongate holes 69 of the pressure member. In this configuration, the pressure member 6 can move along an axial distance which is limited by the abutment of the pins 59 against the lower end of the elongate holes 69. The outer ring 7 is mounted from the lower end 5*b* onto the receiving part 5, and is oriented with respect to the receiving part 5 such that the elevations 71 with the rod supports 72 are aligned with the U-shaped recess 54 of the receiving part 5. The outer ring 7 is then shifted over the receiving part 5 until the inclined lower surface 70*c* of the protrusion 70 snaps into the groove 500 and hooks into the inclined lower surface 500*c* of the groove 500. As a result, the outer ring 7 is secured against removal in a direction towards the lower end 5*b* of the receiving part and/or against rotation.

Figures 24A, 24B, 24C, 24D, 24E, 24F:
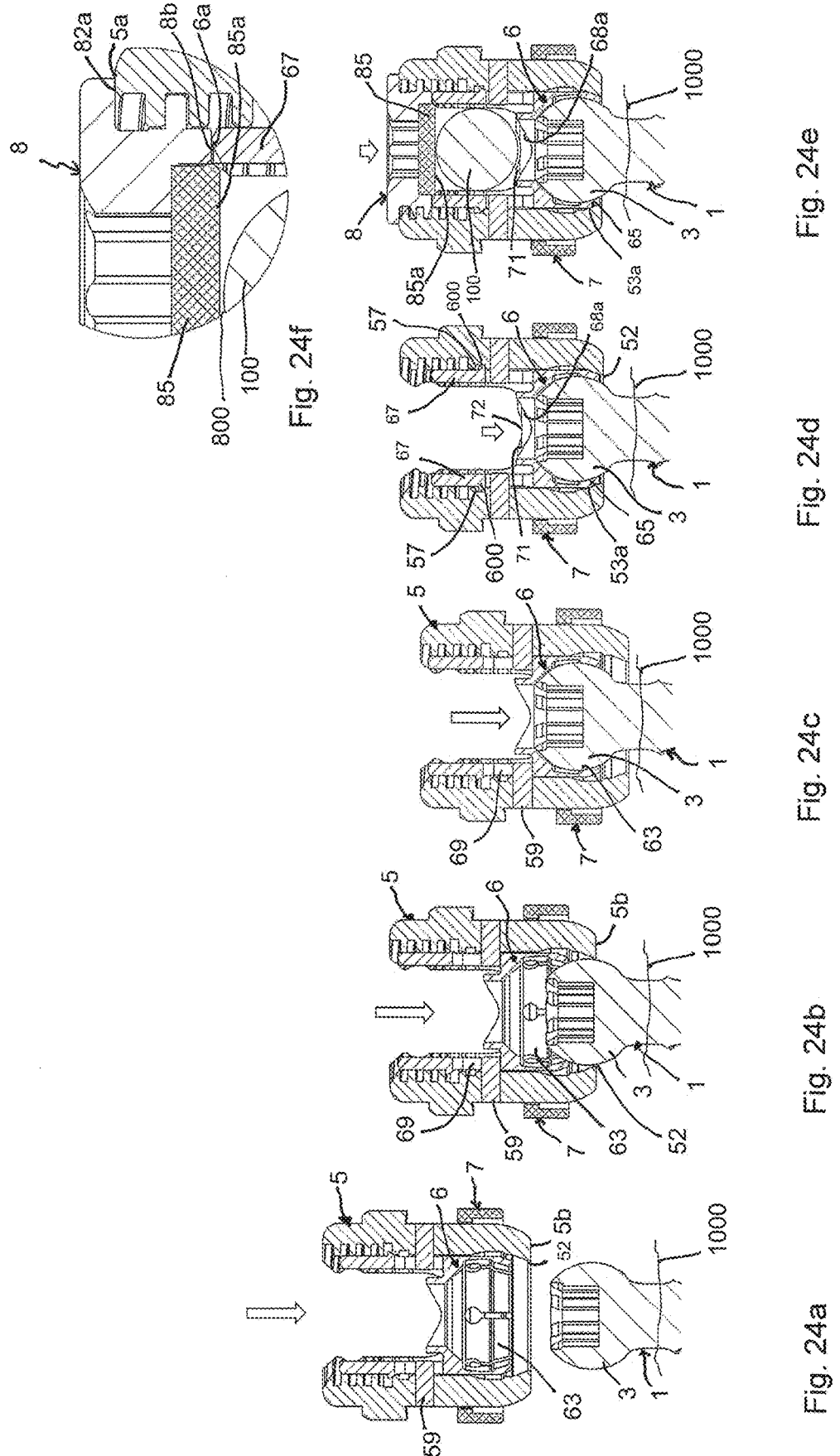

In use, referring to FIGS. 24*a* to 24*f*, the receiving part 5 which is pre-assembled with the pressure member 6 and the outer ring 7 is configured to be connected to the bone anchoring element 1. In a first method of use, the bone anchoring element 1 has been inserted into a bone part or a vertebra 1000 prior to coupling the receiving part 5 to the head 3, as shown in FIG. 24*a*. The head 3 of the bone anchoring element 1 projects out of the bone surface and the pre-assembled receiving part is placed with the lower end 5*b* towards the head 3, as shown in FIG. 24*b*. When the head 3 enters into the head receiving recess 63, the pressure member 6 is moved upwards in the passage 51 until further upward movement is limited by the pins 59. The flexible second portion 62 of the pressure member 6 expands in the accommodation space 53 and snaps onto the head 3, as shown in FIG. 24*c*. Thereafter, the receiving part 5 is pulled slightly away from the head and the pressure member 6, so that the cooperating surfaces 53*a* of the receiving part 5 and 65 of the pressure member 6 engage to preliminarily hold the head in the receiving part in a pivotable manner, as shown in FIG. 24*d*. This is a pre-locking position where the head 3 is prevented from removal through the lower opening 52. In the pre-locking position of the pressure member 6, the projections 600 on the legs 67 are located in the grooves 57 of the receiving part 5 and prevent upward movement of the pressure member 6 out of the pre-locking position. It shall be noted that the size of the head and the head receiving recess may be selected such that, in the pre-locking position of the pressure member 6, the head may be temporarily held by friction at a particular angular position and can be pivoted to another angular position when applying a force to overcome the frictional force, such as manually pivoting the receiving part relative to the head, at which point the head may be held again by friction at the new angular position.

Referring in greater detail to FIG. 24*d*, the outer ring 7 projects with the elevations 71 and the first rod contact surface 72 at least partially above the second rod contact surface 68*a* of the pressure member 6.

Referring to FIGS. 24*e* and 24*f*, the rod 100 is inserted and the fixation member 8 is screwed between the legs 55 of the receiving part 5. The rod 100 rests on the first rod contact surface 72 of the outer ring 7. FIG. 24*f* shows the small gap 800 between the upper surface of the rod 100 and the lower surface 85*a* of the fixation member 8. As the fixation member 8 abuts against the upper end 5*a* of the receiving part 5, the rod 100 remains freely movable in a direction of the rod axis within the receiving part. At the same time, the head 3 remains pivotable with respect to the pressure member 6 and the receiving part 5. The lower surface 8*b* of the fixation member preferably does not exert an axial force onto the pressure member 6.

In an alternative method of use, the bone anchoring element 1 can be coupled to the receiving part 5 prior to insertion of the shank 2 into bone.

The fixation member 8 can be used to produce a bone anchoring device that allows movement of the rod and movement of the head in the receiving part at the same time. This could be used, for example, in a growing rod construct. This creates further possibilities of correction steps in which it may be advantageous to keep the receiving part pivotable relative to the shank.

Referring to FIGS. 25 to 27, a second embodiment of the bone anchoring device includes the second fixation member 8'. All other parts are identical or very similar to the first embodiment. The second fixation member 8' is similar to the first fixation member except that it lacks the flange 82, and therefore can be screwed deeper into the rod channel. All parts and portions of the second fixation member that are identical or very similar to those of the first fixation member are marked with the same reference numerals, and the descriptions thereof are not repeated. A maximum outer width of the second fixation member is defined by the outer diameter of the thread 83. The surface at the lower end 8*b* in this embodiment may be concavely shaped to match the corresponding convexly shaped upper end surface of the legs of the pressure member 6. In greater detail, the surface at the lower end 8*b* of the second fixation member 8' has an inclined inner surface 801 that may in a cross-sectional view be longer than an inclined outer surface 802, which in combination are concavely roof-shaped. The convexly shaped upper end surfaces 601, 602 of the pressure member and the concavely shaped matching end surfaces 801, 802 fit together when the second fixation member is screwed between the legs 55 of the receiving part. Thereby, the connection in the radial direction is improved and a radial play that could lead to an inhomogeneous pressure onto the pressure member 6 may be reduced.

An axial length of the second fixation member 8' is such that when the second fixation member is tightened, the second fixation member 8' presses onto the pressure member 6 so that the pressure member 6 is moved downwards until the cooperating surfaces 65 of the pressure member 6 and 53*a* of the receiving part 5 engage to clamp the head 3. In this configuration as shown in FIG. 27, the rod 100 rests on the outer ring 7 while a gap 800 remains between the lower surface 85*a* of the insert member 85 and the upper surface of the rod, such that the rod can still slide within the receiving part.

Referring to FIGS. 28 to 30, a third embodiment of the polyaxial bone anchoring device includes the third fixation member 8''. The third fixation member is a set screw with an upper end 8*a* and a lower end 8*b*, and a tool engagement recess 81 that extends from the upper end 8*a* towards the lower end 8*b*. The third fixation member 8'' further has a projection 86, preferably a cylindrical projection, at the lower end 8*b*, with a free end surface 86*a*. An outer width of the projection 86 is smaller than an inner width of the pressure member 6 between the legs 67. Thus, when the third fixation member 8'' is inserted between the legs 55 of the receiving part 5, the projection 86 can be advanced between the legs 67 of the pressure member 6 without touching the pressure member 6. The length of the projection 86 in the axial direction is such that when the third fixation member 8'' is inserted between the legs 55 of the receiving part 5, the lower surface 86*a* of the projection 86 presses onto the surface of an inserted rod 100. When the third fixation member 8'' exerts pressure onto the rod 100, the rod in turn exerts pressure onto the outer ring 7. The outer ring 7 is deformed until the rod rests on the rod contact surface 68*a* of the pressure member 6. The rod may simultaneously still contact the first rod support surface 72 of the outer ring.

Hence, the outer ring 7 is configured to change between a first configuration and a second configuration. In the first configuration, the outer ring 7 is non-deformed and the elevations 71 of the outer ring 7 project above the second rod contact surface 68*a* of the pressure member 6. In the second configuration, the outer ring 7 is deformed and the elevations 71 with the first rod contact surface 72 no longer extend above the second rod contact surface 68*a* of the pressure member 6, such that the rod 100 rests on the second rod contact surface 68*a* of the pressure member 6. The deformation is reversible. This means that when the pressure from the rod onto the outer ring 7 is relieved, the outer ring 7 re-assumes the first configuration.

In use, as depicted in FIG. 30, tightening the third fixation member 8'' results in an axial force via the projection 86 onto the inserted rod 100. As a result, while tightening the third fixation member 8'', the head 3 and the rod 100 are locked in the receiving part 5 simultaneously.

Figures 31, 32:
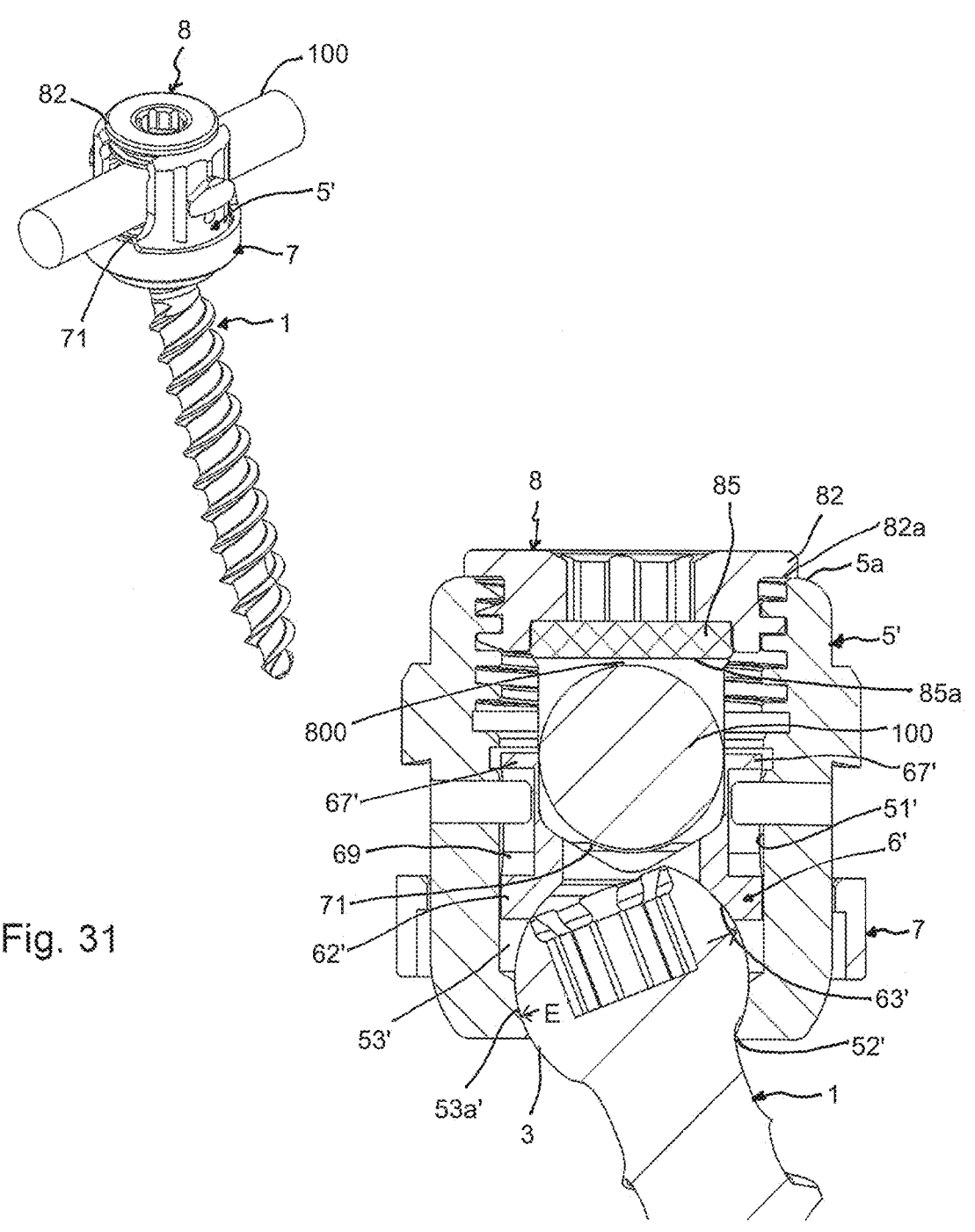
FIG. 31 shows a perspective view of a second embodiment of a polyaxial bone anchoring device with the first fixation member in an assembled state.
FIG. 32 shows a cross-sectional view of the polyaxial bone anchoring device of FIG. 31, the cross-section taken in a plane perpendicular to a longitudinal axis of a rod channel and extending through centers of legs of a receiving part of the polyaxial bone anchoring device.

Referring to FIGS. 31 and 32, a still further embodiment of the polyaxial bone anchoring device is described. The polyaxial bone anchoring device in this embodiment differs from the embodiments of FIGS. 1 to 30 in the design of the pressure member and the receiving part. The receiving part 5' includes, adjacent to the lower end 5*b*, a seat 53*a'* for the head 3 of the bone anchoring element 1, in which the head 3 is pivotably supported. The lower opening 52' has an inner diameter that is smaller than the greatest diameter E of the head 3. Thus, in this embodiment, the bone anchoring element 1 has to be inserted from the upper end 5*a* of the receiving part and guided with the shank 2 through the lower opening 52' until the head 3 rests in the seat 53*a'*. The accommodation space 53' is configured to accommodate a portion of the head 3 and a portion of the pressure member 6'. The pressure member 6' has a lower portion 62' with a spherical recess 63' that is configured to cover the head 3 above the region with the greatest outer diameter E and to exert pressure onto the head 3. The lower portion 62' has a substantially cylindrical outer surface and is configured to move in the passage 51' of the receiving part 5'. It shall be noted that the seat 53*a'* may also have any shape that allows the head 3 to pivot therein like a ball and socket joint. For example, the seat 53*a'* may also be conically-shaped.

Since the bone anchoring device according to FIGS. 31 and 32 is a top-loading bone anchoring device in which the anchoring element 1 is inserted from the upper end 5*a* into the receiving part 5', the polyaxial bone anchoring device can be inserted into bone with the receiving part 5', the pressure member 6', the bone anchoring element 1, and the outer ring 7 pre-assembled. In the figures, the first fixation member 8 is shown in use with the polyaxial bone anchoring device. When the fixation member 8 is tightened, the rod rests on the outer ring 7 and is still movable since there is the gap 800 between the uppermost surface of the rod and the lower surface 85*a* of the insert 85. The pressure member 6' may have shorter legs 67' that do not project over the rod surface. Hence, the pressure member 6' does not exert pressure onto the head 3. Thus, in the embodiment shown in FIGS. 31 and 32, the head 3 remains pivotable and the rod 100 remains movable when the first fixation member is tightened.

Using the third fixation member 8" of FIGS. 28 and 29 allows fixation of the rod and the head simultaneously by pressing the projection 86 onto the rod, which in turn presses onto the pressure member 6', thereby also locking the head 3.

In a further modification of this embodiment, the pressure member 6' also includes legs that extend above the uppermost surface of an inserted rod. Hence, in such a modification, the second fixation member 8' according to FIGS. 25 and 26 can also be used to lock the head while leaving the rod movable.

Figures 33, 34:
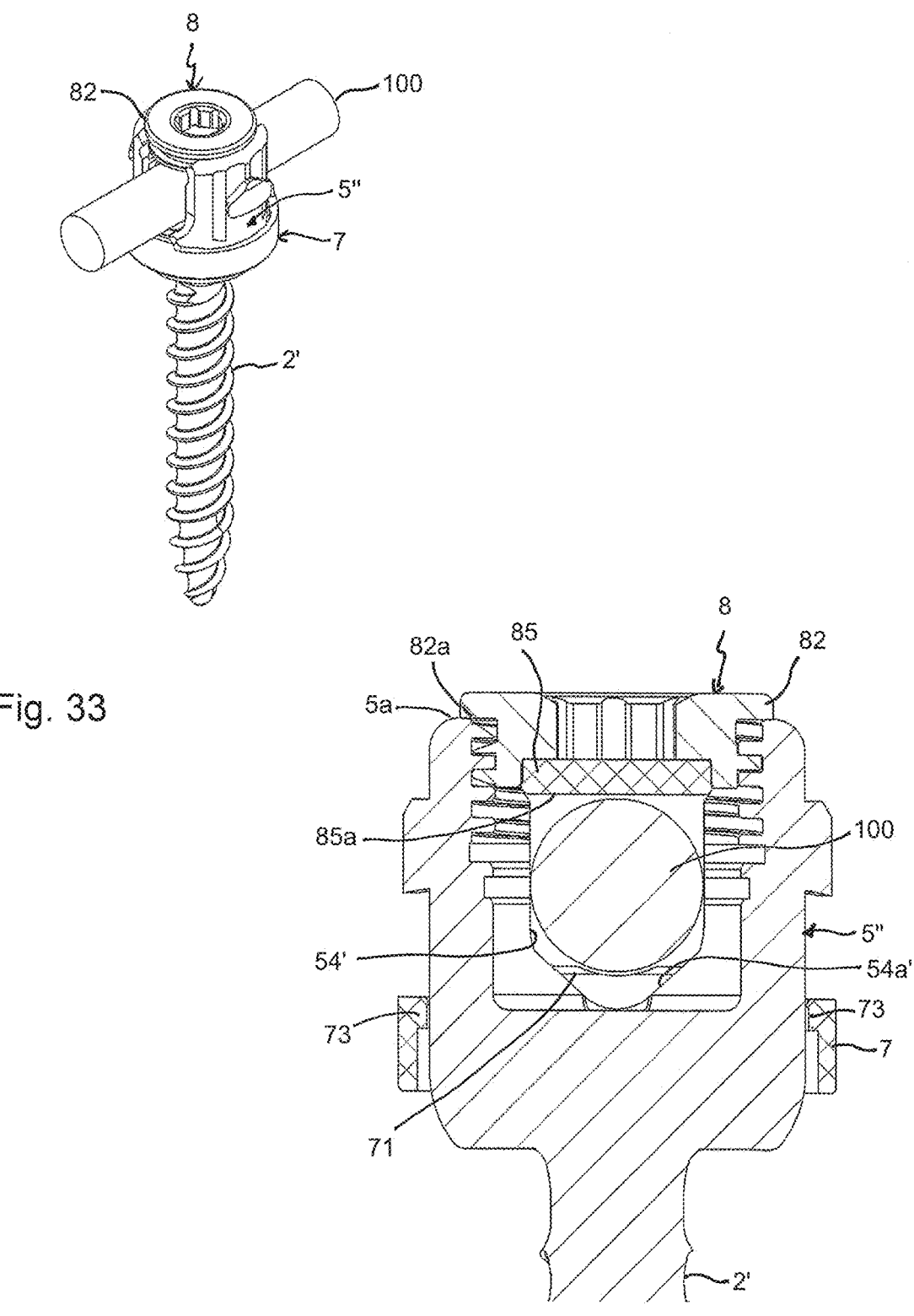
FIG. 33 shows a perspective view of a third embodiment of a bone anchoring device in the form of a monoaxial bone anchoring device with the first fixation member in an assembled state.
FIG. 34 shows a cross-sectional view of the bone anchoring device of FIG. 33, the cross-section taken in a plane perpendicular to a longitudinal axis of a rod channel and extending through centers of legs of a receiving part of the bone anchoring device.

Referring to FIGS. 33 and 34, a further embodiment of the bone anchoring device is described. The bone anchoring device in this embodiment is a monoaxial bone anchoring device. This means, that the shank 2' and the receiving part 5" are not pivotable with respect to each other. The receiving part 5" has an outer appearance that is very similar to that of the receiving part 5 and 5' of the previous embodiments. The shank 2' is, in this embodiment, monolithic with the receiving part 5". A second rod support is formed by the bottom 54a' of the substantially U-shaped recess 54 that defines the channel for receiving the rod. As shown in FIG. 34, the second rod contact surface 54a' has a substantially V-shaped contour, preferably with a rounded bottom for receiving rods having different diameters. The outer ring 7 projects at least partially with the extensions 71 above the second rod contact surface 54a', so that the rod 100 can rest on the first rod contact surface 72 of the outer ring 7.

The bone anchoring device is shown with the first fixation member 8. Therefore, when the first fixation member 8 is tightened, the rod 100 is still movable in the rod channel and can slide along the lower surface 85a of the third fixation member and on the first rod contact surface 72 of the outer ring 7.

Alternatively, when the third fixation member 8" is used, the projection 86 presses onto the rod when the third fixation member 8" is tightened. As a result, the outer ring is deformed and the rod 100 is pressed against the second rod contact surface 54a' of the receiving part 5". Hence, by selecting a suitable fixation member, the monoaxial bone anchoring device can be used as a bone anchoring device that allows the rod to freely slide or as a bone anchoring device which is configured to fix the rod thereto.

Further modifications of the above described embodiments are also conceivable without departing from the spirit and scope of the invention. In particular, the shapes of the respective parts are not limited to the detailed shapes shown in the figures. Deviations may be possible and encompassed by the disclosure. The variable configuration member is shown as a closed ring. However, the variable configuration member in alternative embodiments can also be a member that is, for example, partially arranged in the rod channel and is deformable upon pressure exerted by the rod onto it.

Also, a two-part fixation member may be included in the system, with an outer member and an inner member. The receiving part and the pressure member are not limited to the detailed shapes shown. The receiving part and/or the pressure member may also have two-part designs. The rod contact surface in the pressure member may be flat or cylindrical. Also, the pressure member in the first embodiment can have short legs that do not project above a surface of an inserted rod. Also, the receiving part may have extended tabs which prolong the legs. Such a receiving part may be used, for example, for reduction procedures in which vertebrae or bone parts are re-aligned.

In a further modification, the receiving part can be designed to have two rod channels, so that two sliding rods may be employed. With the selection of a suitable fixation member, one or both rods can be fixed.

For the bone anchoring element, all types of bone anchoring elements that are suitable for anchoring in bone or a vertebra may be used, in particular, also bone nails.

The rod may have various shapes and/or varying cross-sections along its length. The rod may be stiff or more flexible. The rod may also be, for example, a cord or a tether.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device for anchoring a rod to a bone or vertebra, the bone anchoring device comprising:
a bone anchoring element comprising a shank and a head;
a receiving part having a first end, a second end below the first end, a central axis extending between the first and second ends, a channel at the first end for receiving the rod, and an accommodation space at the second end for accommodating the head of the bone anchoring element;
a pressure member movable in the receiving part to directly engage and exert pressure on the head, wherein a portion of the pressure member is configured to extend to an axial position that is lower than an axial position of a greatest diameter of the head measured in a direction perpendicular to the central axis; and
a separate ring-shaped member configured to be assembled to and movable relative to the receiving part;
wherein when the head, the pressure member, and the ring-shaped member are assembled to the receiving part and when the ring-shaped member is at a first configuration, the ring-shaped member is configured to block the pressure member from being moved axially downwardly towards the second end of the receiving part; and
wherein the ring-shaped member is adjustable from the first configuration to a second configuration where at least part of the pressure member is movable axially downwardly past at least part of the ring-shaped member to increase the pressure exerted on the head.

2. The bone anchoring device of claim 1, wherein at least part of the ring-shaped member is deformable for adjusting the ring-shaped member from the first configuration to the second configuration.

3. The bone anchoring device of claim 2, wherein the at least part of the ring-shaped member is elastically deformable.

4. The bone anchoring device of claim 1, wherein the ring-shaped member is positionable around the receiving part.

5. The bone anchoring device of claim 1, wherein the ring-shaped member comprises a rod contacting surface configured to extend into the channel to engage the rod and to block the rod from engaging the pressure member when the ring-shaped member is at the first configuration.

6. The bone anchoring device of claim 1, wherein part of the pressure member is configured to extend into the channel to engage the rod.

7. The bone anchoring device of claim 1, wherein when the ring-shaped member is at the first configuration, the head is pivotable relative to the receiving part.

8. The bone anchoring device of claim 1, wherein the ring-shaped member is configured to be spaced apart from the head.

9. The bone anchoring device of claim 1, wherein the pressure member and the ring-shaped member are devoid of any axial abutments relative to one another at least when the ring-shaped member is at the second configuration.

10. A bone anchoring device for anchoring a rod to a bone or vertebra, the bone anchoring device comprising:

a bone anchoring element comprising a shank and a head;

a receiving part having a first end, a second end below the first end, a central axis extending between the first and second ends, a channel at the first end for receiving the rod, and an accommodation space at the second end for accommodating the head of the bone anchoring element;

a pressure member movable in the receiving part to directly engage and exert pressure on the head; and a separate deformable member configured to be assembled to and movable relative to the receiving part;

wherein when the head, the pressure member, and the deformable member are assembled to the receiving part and when the deformable member is at a first configuration, the deformable member is configured to block the pressure member from being moved axially downwardly towards the second end of the receiving part; and wherein the deformable member is deformable from the first configuration to a second configuration where the pressure member is movable axially downwardly to increase the pressure exerted on the head, while the deformable member is configured to be spaced apart from the head, and while the pressure member and the deformable member are devoid of any axial abutments relative to one another.

11. The bone anchoring device of claim 10, wherein the deformable member is elastically deformable.

12. The bone anchoring device of claim 10, wherein the deformable member is positionable around the receiving part.

13. The bone anchoring device of claim 10, wherein the deformable member comprises a rod contacting surface configured to extend into the channel to engage the rod and to block the rod from engaging the pressure member when the deformable member is at the first configuration.

14. The bone anchoring device of claim 10, wherein part of the pressure member is configured to extend into the channel to engage the rod.

15. The bone anchoring device of claim 10, wherein when the deformable member is at the first configuration, the head is pivotable relative to the receiving part.

16. The bone anchoring device of claim 10, wherein when the deformable member is at the second configuration, the pressure member is movable further axially downwardly to further increase the pressure exerted on the head.

17. The bone anchoring device of claim 10, wherein when the deformable member is at the second configuration, at least part of the pressure member is movable to a same axial position as at least part of the deformable member.

* * * * *